(12) United States Patent
Falck, Jr. et al.

(10) Patent No.: US 7,479,109 B2
(45) Date of Patent: *Jan. 20, 2009

(54) OPHTHALMOLOGIC APPLANATION CORNEA CONTACTOR REPLACEMENT SYSTEM FOR EYE EXAMINING INSTRUMENT

(75) Inventors: Francis Y Falck, Jr., Stonington, NY (US); Robert W Falck, Pawcatuck, CT (US)

(73) Assignee: Falck Medical, Inc., Mystic, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/930,508

(22) Filed: Oct. 31, 2007

(65) Prior Publication Data

US 2008/0077000 A1  Mar. 27, 2008

Related U.S. Application Data

(63) Continuation of application No. 11/420,946, filed on May 30, 2006, now abandoned, which is a continuation of application No. 10/453,253, filed on Jun. 3, 2003, now Pat. No. 7,153,267.

(51) Int. Cl.
*A61B 3/16* (2006.01)

(52) U.S. Cl. .................................... 600/406; 600/405
(58) Field of Classification Search .................. 600/398, 600/405, 406; 359/831; 351/200
See application file for complete search history.

(56) References Cited

U.S. PATENT DOCUMENTS 7,153,267 B2 * 12/2006 Falck et al. .................. 600/406

* cited by examiner

*Primary Examiner*—Max Hindenburg
*Assistant Examiner*—Jonathan M Foreman
(74) *Attorney, Agent, or Firm*—Brown & Michaels, PC

(57) ABSTRACT

A replaceable cornea contactor for an eye examining instrument is made to be discarded after each use. A bendable tab molded on the cornea contactor is deformed by a strain gauge as the cornea contactor is inserted into a cornea contactor holder, and a signal from the strain gauge is used to verify that a previously unused cornea contactor has been inserted into the holder. A microprocessor is programmed to recognize the signal produced by initial deformation of the cornea contactor tab so as to proceed with an eye examination only after receiving the strain gauge signal verifying that a previously unused cornea contactor has been inserted.

18 Claims, 6 Drawing Sheets

OPHTHALMOLOGIC APPLANATION CORNEA CONTACTOR REPLACEMENT SYSTEM FOR EYE EXAMINING INSTRUMENT

RELATED APPLICATION

This is a continuation-in-part patent application of application Ser. No. 11/420,946 filed 30 May 2006, entitled "Opthalmologic Applanation Prism Replacement System"; which is abandoned upon filing of this application, and which in turn is a continuation-in-part of application Ser. No. 10/453,253, filed 3 Jun. 2003, entitled "Opthalmologic Applanation Prism Replacement System". The aforementioned applications are incorporated herein by reference.

FIELD OF THE INVENTION

Eye examining instruments using cornea contactors.

BACKGROUND

For eye examining instruments that contact a cornea, it is desirable to discard and replace a cornea contactor after it has become wetted with tears of a pair of eyes being examined. Discarding used cornea contactors can prevent transfer of bacteria, viruses or prions from one patient to another. For this purpose, our previous U.S. Pat. Nos. 5,070,875, 6,179,779, and 6,471,647 and our pending application Ser. Nos. 09/811,709 and 10/178,987 have suggested a few ways of making tonometer prisms readily replaceable. The desirability of replacing cornea contactors is not limited to tonometers or prisms, though. As revealed in our application Ser. No. 10/178,987, eye contacting cornea contactors are also useable in opthalmologic instruments examining eyes for purposes other than tonometry. Also, corneal contactors are not limited to prisms, and can be formed as windows or other light transmitting elements that contact a cornea for examination purposes.

SUMMARY

The invention of this application involves an improved form of replaceable cornea contactor and a new interaction or interrelationship between a cornea contactor and a tonometer or other eye examining instrument arranged to ensure that the cornea contactor is replaced after each examination of a pair of eyes. The cornea contactor and its interaction with the instrument that holds it are aimed at low cost and simplicity so that cornea contactor replacement will not be unduly expensive in material, time or labor. Making cornea contactor disposal and replacement convenient and efficient helps ensure that cornea contactors will actually be replaced rather than reused with possible risk to patients.

To accomplish this the invention involves a configuration of a disposable cornea contactor that is molded of resin to operate within an instrument having a microprocessor and a cornea contactor holder into which the cornea contactor is inserted in a way that requires cornea contactor replacement before proceeding with an eye examination. The cornea contactor has a molded element formed to extend transversely of a direction of insertion of the cornea contactor into the holder, and the element is deformable from an initial position to a deformed position as the cornea contactor reaches an operating position within the holder. The element is also configured so that its first deformation requires a distinct stress not required for any subsequent deformation. Deformation of the element is accomplished by a strain gauge positioned in the holder to engage the element and produce a signal representing the strain encountered in deforming the element as the cornea contactor is inserted into the holder. The microprocessor is programmed to recognize the strain gauge signal representing the first deformation of the element and to proceed with an eye examination only when insertion of the cornea contactor into the holder causes the strain gauge to produce the signal representing the first deformation of the element.

DRAWINGS

DETAILED DESCRIPTION

Figure 1:
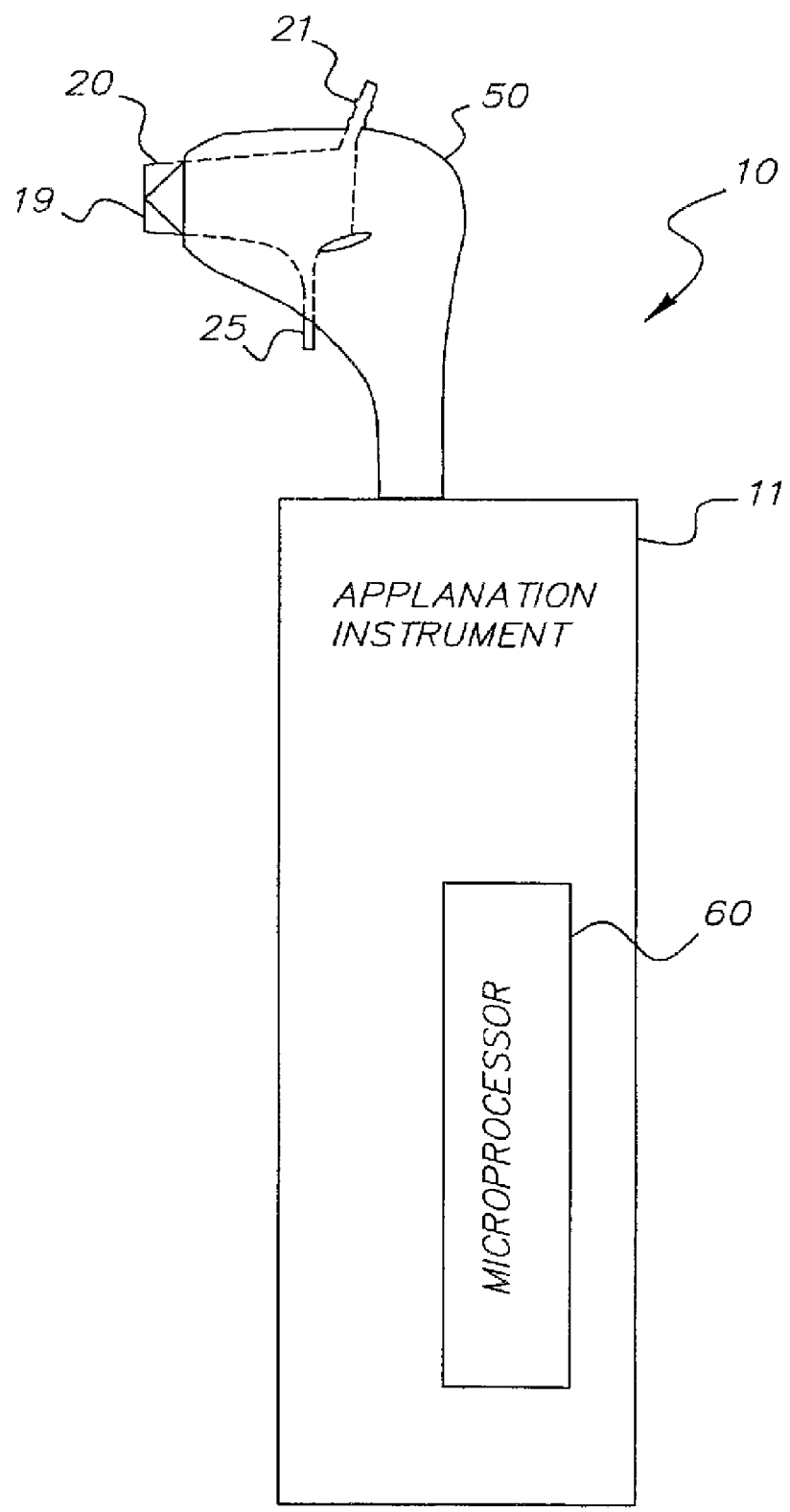
FIG. 1 is a partially schematic elevational view of a preferred embodiment of cornea contactor and cornea contactor holder combined with a schematically represented instrument.

An eye examining instrument 10, as shown schematically in FIG. 1 is designed for applanation tonometry and includes an applanating cornea contactor 20, a cornea contactor holder 50 and a microprocessor 60. Instrument 10 can be an applanation tonometer such as disclosed in our previous U.S. Pat. Nos. 5,070,875 and 6,179,779. Beyond this, however, cornea contactors and cornea contactor holders are also useful in other eye examining instruments for measuring eye properties other than intra ocular pressure. As explained in our application Ser. No. 10/178,987, such instruments, can use cornea contactors for measuring ocular blood flow, tonography, and different aspects of intra ocular pressure measurements such as systolic pressure, diastolic pressure, and average or mean intra ocular pressure. For purposes of this invention, what is important is not what measurement instrument 10 is being used for, but the configurations and interactions between cornea contactor 20, and holder 50. Also unimportant is the optical or metrologic properties of cornea contactor 20, which can be any energy transmitting device having a surface that contacts the eye.

A body 11 of instrument 10 is schematically illustrated in FIG. 1, because it not only can have many different shapes but also preferably uses different shapes for different purposes.

For example, body 11 can have one shape when mounted on and powered by a slit lamp microscope, and can have a different shape configured as a battery powered, hand held portable instrument. Shapes for body 11 made suitable for either of these purposes can also vary widely for other reasons involving materials, costs, and appearance.

Cornea contactor 20 is preferably molded of resin material to be inexpensive and thus affordably replaceable. Cornea contactor 20 is also configured to be easily inserted into and removed from holder 50 so that discarding cornea contactor 20 after each use is convenient as well as affordable. Finally, as explained below, cornea contactor 20 and holder 50 are configured so that instrument 10 can reliably determine that a previously unused cornea contactor 20 is positioned in holder 50 before proceeding with an eye examination. This ensures that cornea contactor 20 is actually replaced for each successive patient.

Cornea contactor 20 can be formed in many ways for different examination purposes. It is preferably molded of resin material to be affordably disposable. If contactor 20 is used for corneal applanation measurements, it preferably has a flat surface disposed to engage a cornea. If contactor 20 is to transmit light for examination and measurement purposes, it is preferably formed of transparent or translucent material. What all the variations of corneal contactor shapes have in common is that the contactor engages the cornea for an examining or measuring purpose after which the contactor is discarded and replaced by a fresh cornea contactor.

For ease of insertion and removal, cornea contactor 20 preferably has an integrally molded gripping tab 21. An eye contacting surface 19 of cornea contactor 20 should not be touched or handled as a fresh cornea contactor is inserted into holder 50, and we prefer that cornea contactor 20 has a gripping tab 21 arranged to be handled while inserting and removing cornea contactor 20. The position and orientation of gripping tab 21 depends partly on the direction and orientation of the cornea contactor insertion and removal motions. Since we prefer lowering cornea contactor 20 downward into holder 50 from above, we also prefer that gripping tab 21 be conveniently arranged to extend upward from cornea contactor 20. In such a position, tab 21 is disposed to be gripped by a thumb and finger for conveniently pushing cornea contactor 20 downward into holder 50, and for lifting cornea contactor 20 upward out of holder 50 after it has been used. Gripping tab 21 can also be configured in different ways and arranged in different positions, depending partly upon the most convenient way chosen for inserting and removing cornea contactor 20.

The proper location of cornea contactor 20 when it is inserted into holder 50 is also important. An improperly seated cornea contactor 20 could fail to produce operable results. To prevent this we prefer a cornea contactor locating and detenting system that not only ensures proper seating of an inserted cornea contactor, but also lets a person inserting the cornea contactor know when proper seating has occurred. For these purposes, preferred cornea contactor 20 has a location projection 25 that extends downwardly from cornea contactor 20 in an opposite direction from gripping tab 21 to locate the cornea contactor properly in holder 50. A different position or orientation for projection 25 is also possible, especially for a cornea contactor that is inserted into holder 50 in a different way.

Figure 8:
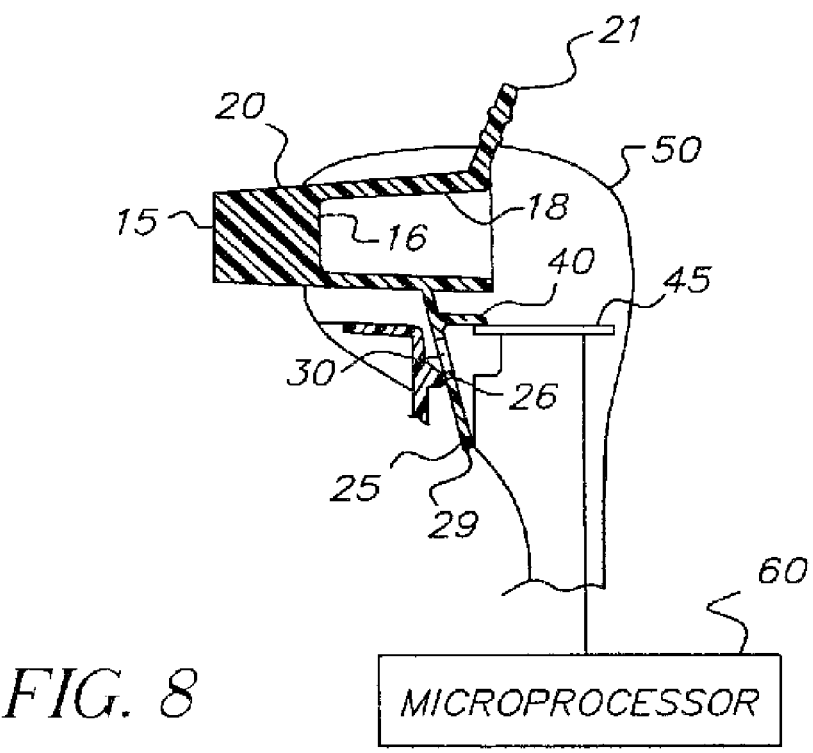
FIG. 8 is a partially schematic and fragmentary cross sectional view of the cornea contactor and holder of FIG. 7, showing the cornea contactor being inserted part way into the holder.
Figure 9:
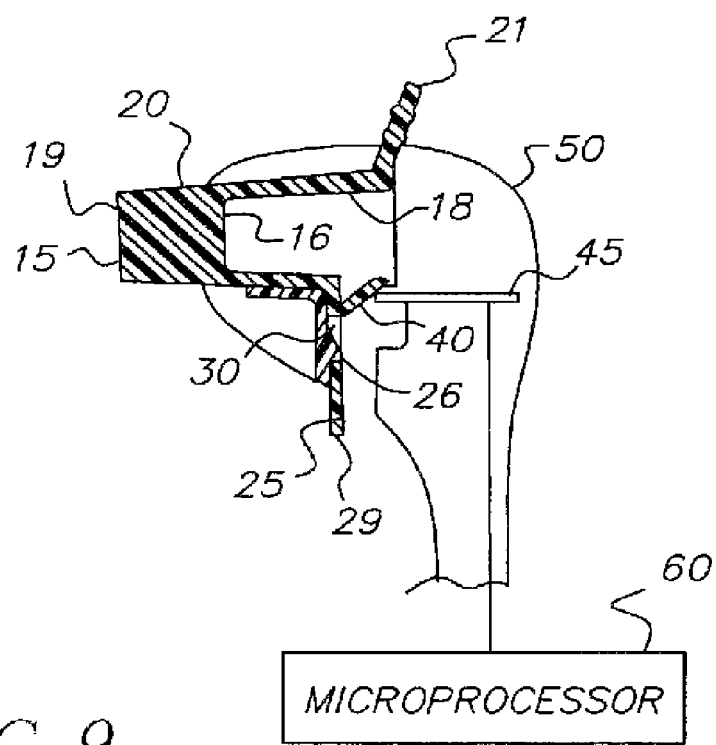
FIG. 9 is a partially schematic and fragmentary cross sectional view of the cornea contactor and holder of FIG. 7, taken along the line 9-9 thereof, and showing the cornea contactor fully inserted into the holder.

Projection 25 also preferably detents or snap locks into place when cornea contactor 20 is properly positioned. FIGS. 8 and 9 best show this action of location tab 25. Cornea contactor 20 is shown partially inserted into holder 50 in FIG. 8, where location projection 25 is sliding over detent 26. To ease this motion, detent 26 has a cammed entry surface 27. After cornea contactor 20 is fully seated in holder 50, as shown in FIG. 9, an aperture or opening 30 in locator projection 25 snaps over and locks against detent 26 to hold cornea contactor 20 firmly in an operating position.

Removing cornea contactor 20 after it has been used in examining a pair of eyes requires pulling back on the lower tip 29 of location tab 25 to release its locking engagement with detent 26. Cornea contactor 20 can then be lifted out of holder 50 by gripping and pulling upward on tab 21. For cornea contactor release purposes, the lower end 29 of location tab 25 preferably extends below the bottom of holder 30, where it is accessible to finger pressure releasing projection 25 from detent 26.

Figure 2:
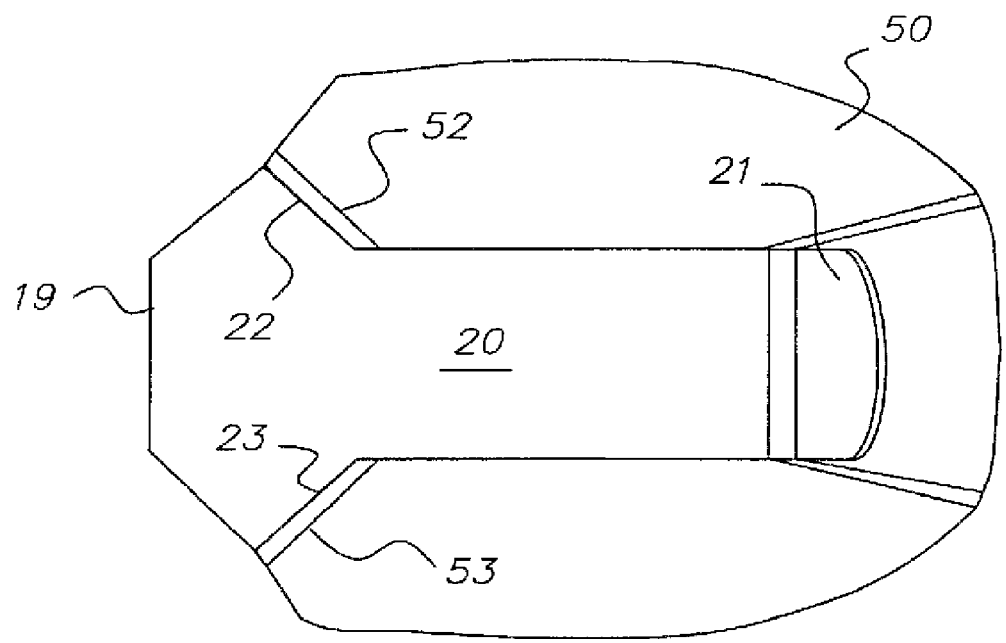
FIG. 2 is a partially schematic plan view of the cornea contactor and holder shown in FIG. 1.
Figure 3:
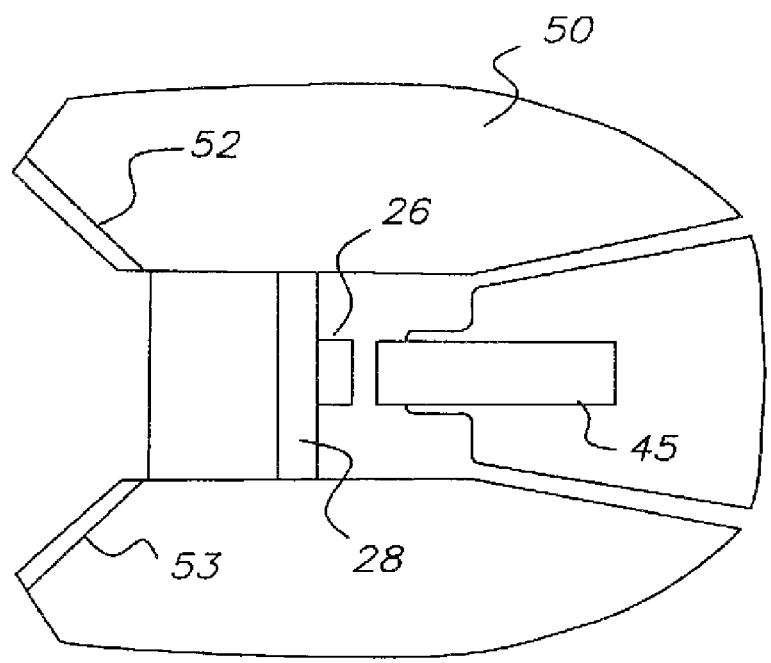
FIG. 3 is a partially schematic plan view of the cornea contactor holder as shown in FIG. 2, with the cornea contactor removed.
Figure 4:
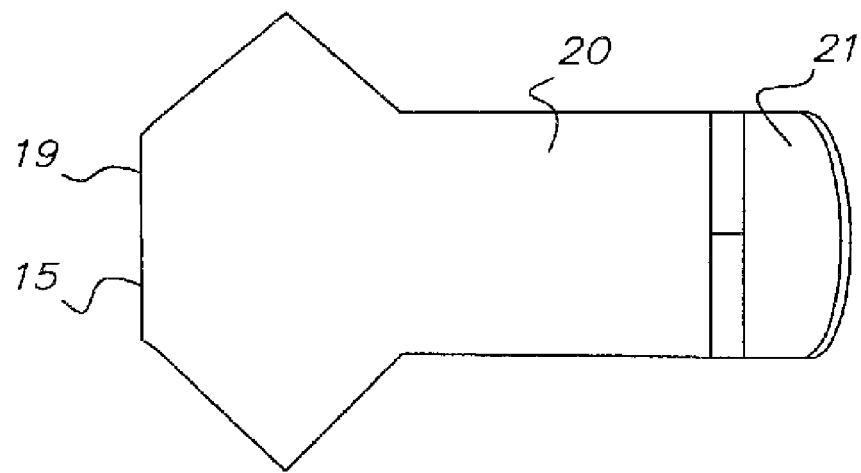
FIG. 4 is a plan view of a preferred embodiment of a cornea contactor combinable with a holder shown in FIGS. 2 and 3 and useable with the instrument of FIG. 1.
Figure 5:
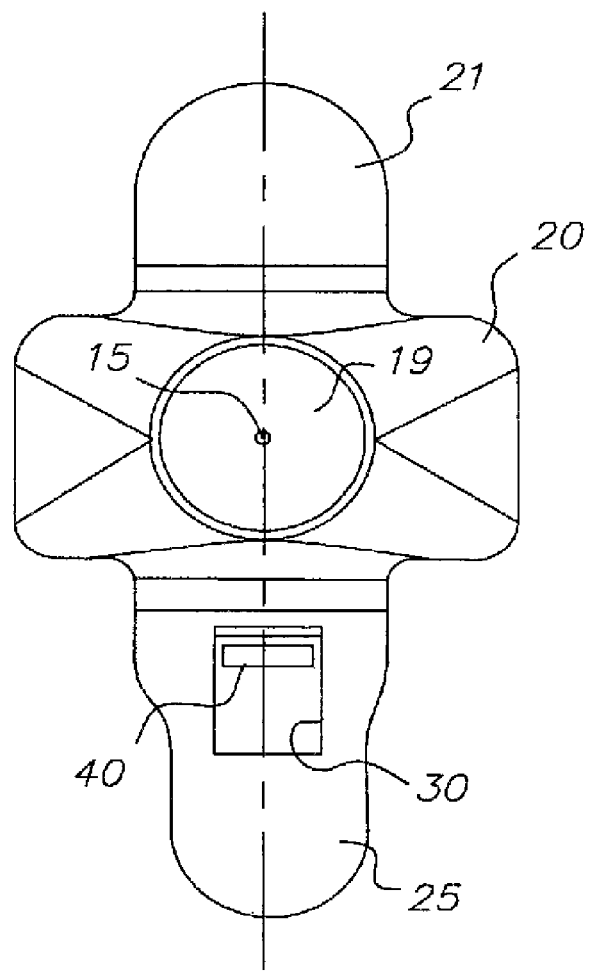
FIG. 5 is a front elevational view of the cornea contactor of FIG. 4.
Figure 6:
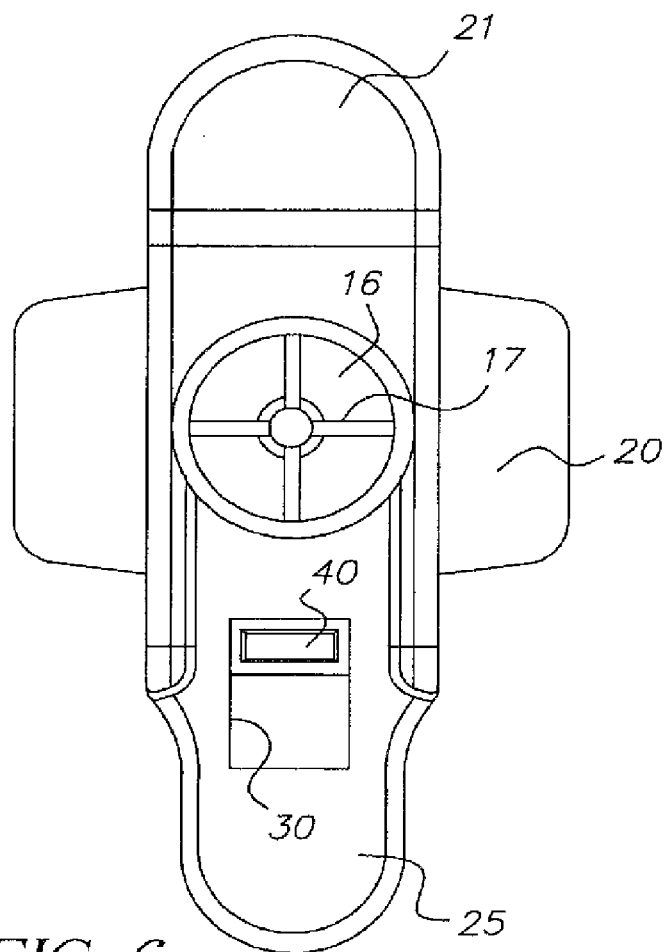
FIG. 6 is a rear elevational view of the cornea contactor of FIG. 5.
Figure 7:
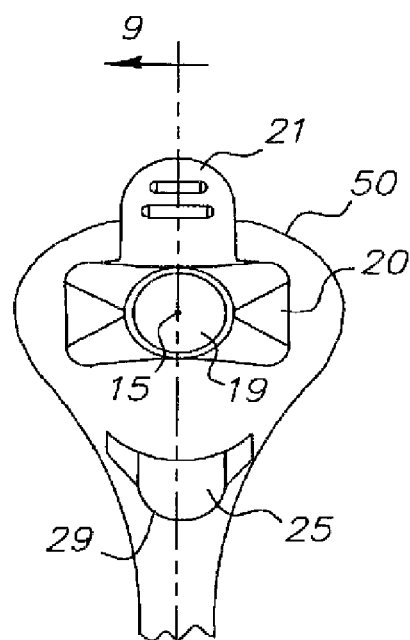
FIG. 7 is a front elevational view of the cornea contactor and holder of FIGS. 1 and 2.

A slot 28 in holder 50 containing detent 26 is angled slightly relative to the orientation of tab 25, which urges location projection 25 rearwardly as cornea contactor 20 is pushed downwardly into holder 50. This draws cornea contactor 20 rearwardly as it is inserted into holder 50 and ensures that cornea contactor port surfaces 22 and 23 are drawn snugly and respectively against emitter 52 and detector 53, which are arranged in holder 50 as shown in FIG. 2. Light from emitter 52 can then reliably enter cornea contactor port 22 to be incident on applanation surface 19 of cornea contactor 20 and be partially reflected to cornea contactor port 23 and detector 53. Cornea contactor ports 22 and 23 are preferably identical so that emitter 52 and detector 53 can be arranged on either side of cornea contactor 20. The amount of light reaching detector 53 depends on the size of an area of cornea applanated by cornea contactor surface 19. The operation and affect of such a light path is explained in our previous U.S. Pat. Nos. 5,070,875 and 6,179,779 and in our application Ser. No. 10/178,987. Cornea contactors can also have different ports and different configurations, depending upon the energy being transmitted and the measurement or observation being made.

There are many different ways that a cornea contactor 20 can be detented or snap locked into a holder 50, other than the particular detent illustrated. What is preferred for any such arrangement is that a detent be positive and noticeable to a person inserting cornea contactor 20, to indicate that the cornea contactor is fully inserted into holder 50. It is also preferred that the detenting of the cornea contactor into the holder be quick and efficient, both for insertion and removal. The detenting system also preferably urges cornea contactor 20 rearwardly to insure that cornea contactor port surfaces 22 and 23 engage emitter 52 and detector 53 in cornea contactor holder 50 for reliable optical operation. The illustrated interlock between tab 25 and detent 26 accomplishes these objectives, but is clearly not the only plausible solution. Different paths of movement for insertion and removal of cornea contactor 20 can lead to different detent systems that accomplish similar objectives.

The interaction between cornea contactor 20 and holder 50 of instrument 10 is also preferably arranged to require that cornea contactor 20 be replaced after each examination of a pair of eyes. The interaction proposed by this invention, is a new way of accomplishing that. The goal is to preclude instrument 10 from examining a new pair of eyes until a new cornea contactor 20 is inserted into holder 50.

The preferred cornea contactor replacement requirement is met by a deformable element 40 integrally formed on cornea contactor 20 to extend transversely of the path of movement followed by cornea contactor 20 as it is inserted into holder 50. Interacting with deformable tab 40 is a strain gauge 45 mounted in holder 50 and communicating with microprocessor 60 in instrument 10. As cornea contactor 20 is inserted into holder 50, deformable tab 40 encounters strain gauge 45, as shown in FIG. 8. As cornea contactor 20 proceeds from a partially inserted position shown in FIG. 8 to a fully inserted position shown in FIG. 9, deformable tab 40 is bent from an initial position shown in FIG. 8 to a deformed position shown in FIG. 9. The bending of deformable element 40 requires stress supplied by the person pushing downward on grippable tab 21 in the course of pushing cornea contactor 20 down into holder 50. Such a stress force is preferably minor and easily achieved by the person inserting cornea contactor 20.

Strain gauge 45, which engages and requires deformation of element 40 as cornea contactor 20 is inserted into holder 50 produces a signal representing the strain encountered in bending tab 40. This signal is delivered to microprocessor 60, which is programmed to recognize a strain signal produced by an initial bending of deformable element 40. Any subsequent bending of element 40 requires a different and preferably reduced strain on gauge 45, which then produces a distinguishably different signal to microprocessor 60. By this arrangement, instrument 10 is able to recognize reliably the insertion of a previously unused cornea contactor 20 into holder 50, because of the distinct signal produced by strain gauge 45 encountering a never previously deformed tab 40. Microprocessor 60 is then programmed to proceed with an eye examination only after receiving the appropriate signal from strain gauge 45 indicating that an unused cornea contactor 20 has been inserted into holder 50.

Figure 10:
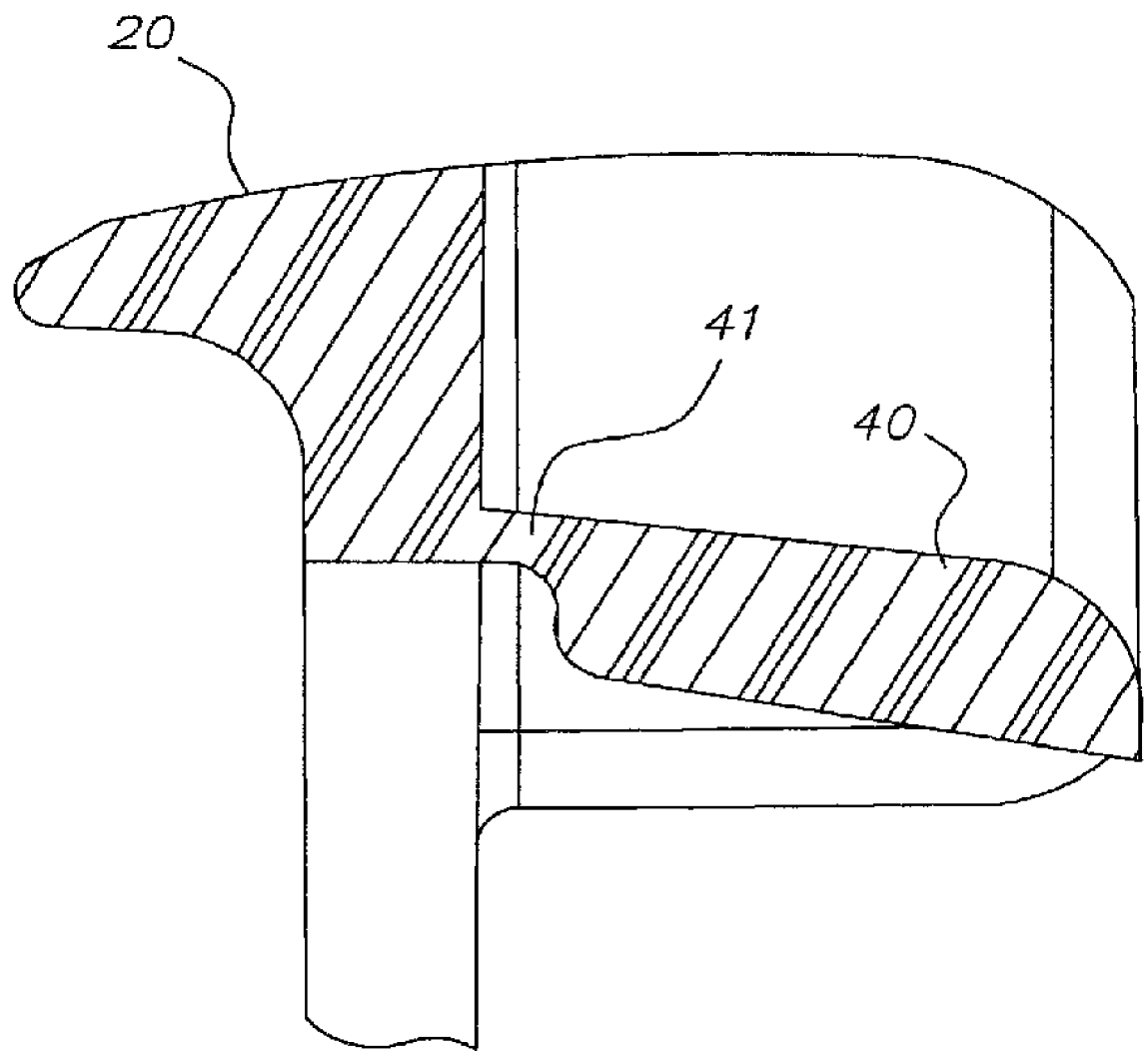
FIG. 10 is an enlarged, fragmentary cross sectional view of a preferred embodiment of a deformable element for the cornea contactor of FIGS. 4-6.

A preferred way of configuring deformable element 40 so that its initial deformation produces a distinct signal from strain gauge 45 is to mold element 40 with a thin hinge connection 41 to cornea contactor 20, as best shown in the enlarged fragmentary view of FIG. 10. Initial bending of element 40 then requires more stress than any subsequent bending of element 40, and this in turn exerts a distinctive strain on gauge 45 during the initial bending of tab 40. Experiments have shown that tape, glue, and other reinforcements of an already-bent tab 40 do not succeed in restoring tab 40 to its initial condition and its initial ability to produce the initial strain signal from gauge 45. From this it appears that the deformable element and strain gauge combination for a cornea contactor replacement requirement cannot be easily defeated.

An advantage of deformable element 40 and strain gauge 45 is that element 40 is not broken away from cornea contactor 20 as it is bent during cornea contactor insertion. Having a cornea contactor element break off and leave a separate piece loose within holder 50 is undesirable, as likely to interfere with operations of holder 50.

Another advantage of deformable element 40 is that it is preferably molded integrally with cornea contactor 20. Experiments have shown that polymers having the desired optical properties for cornea contactor 20 can also provide deformable element 40 so that it co-operates successfully with strain gauge 45, as explained above. This helps make cornea contactor 20 inexpensive, which in turn is desirable to make its discard and replacement affordable.

Deformable elements usable in co-operation with a strain gauge to determine that a replaced cornea contactor has not been previously used can also be arranged in other ways. One configuration we prefer is that the deformable element extends in a direction transverse to the direction of insertion of cornea contactor 20 into holder 50. Changing the direction of the path followed by cornea contactor 20 as it is inserted into holder 50 then changes the preferred direction of orientation of any deformable element. This in turn would change the position of strain gauge 45. It is also not essential that deformable element 40 be a bendable tab, as illustrated. A beam of cornea contactor resin material could be integrally connected at each of its ends to cornea contactor 20 and be deformable in a central region encountered by a strain gauge. Other variations on deformable elements are possible, such as diaphragms or projections that do not bend as far as illustrated. In addition, there are many ways of ensuring that an initial deformation of a molded element exerts a strain on a gauge distinctively different from any subsequent deformation of the element. For example, a bendable element could have a thin molded cornea contactor connection that breaks in one region to allow deformation of another connection that does not break. We prefer that any deformable element be integrally molded with cornea contactor 20, rather than requiring a separate construction attached to cornea contactor 20. Although separately fabricated elements could be made to co-operate successfully with a strain gauge, separate constructions generally cost more and would tend to increase the cost of cornea contactor 20.

Cornea contactors that are preferably replaced after each examination of a pair of eyes can be used in other eye examining instruments such as pachymeters, which measures corneal thickness. Pachymeters can direct energy such as ultrasonic or light waves through a cornea contactor or window contacting an eye while its corneal thickness is measured. Other eye examining instruments can be devoted to measurements of ocular pulse pressure, ocular blood flow, and tonography, such as explained in our pending application Ser. No. 10/178,987, although these functions are preferably combined with a tonometer that measures intraocular pressure.

Cornea contactor 20 is also improved in several other respects. It preferably has a hollow rear region 18, as best shown in FIGS. 8 and 9, to reduce the amount of material required and simplify the molding requirements for cornea contactor 20. Cornea contactor 20 is also preferably made so that an operator can see or sight through cornea contactor 20 to guide it as it approaches a cornea of an eye. For such sighting purposes, rear face 16 of cornea contactor 20 is formed with a reticule 17 identifying a sighting center or cornea contactor axis extending through cornea contactor 20. The applanation face 19 of cornea contactor 20, which is generally flat, is then provided with a small central indent 15 on the optical or sighting axis through cornea contactor 20. Indent 15 does not internally reflect light to detector 53 and thus produces a small dark spot on the front face 19 of cornea contactor 20. A viewer sighting through cornea contactor 20 can then center the dark spot caused by indent 15 within reticule 17 to verify proper alignment of cornea contactor 20 as it approaches the optical center of a cornea of an eye. Indent 15 and reticule 17 are each formed integrally with cornea contactor 20 as it is molded so that neither requires any add on parts. From the patient's point of view, indent 15 on surface 19 appears as a small bright spot. This helps the patient fixate on the center of surface 19 as the cornea contactor approaches the eye. The cornea contactor's sight-through feature for the instrument operator and bright spot fixation feature for the patient, cooperate to help insure accurate coaxial alignment of the eye and the cornea contactor.

What is claimed is:

1. A system ensuring replacement of a molded resin cornea contactor used in an eye examining instrument having a microprocessor and a holder for receiving the cornea contactor in an operating position, the system comprising:

the cornea contactor being molded to have an element that is deformable in a direction of insertion of the cornea contactor into the holder;

a strain gauge arranged in the holder to engage the element as the cornea contactor is being inserted into the holder and before the cornea contactor reaches the operating position;

the strain gauge being arranged to deform the element from its initial position to a deformed position as the cornea contactor is moved fully into the holder to the operating position;

the strain gauge being arranged to produce a strain signal delivered to the microprocessor representing the strain involved in deforming the element from its initial position to its deformed position;

the element being configured so that a first deformation of the element from its initial position to its deformed position requires more stress than any subsequent deformation of the element from its initial position to its deformed position;

the microprocessor being programmed to distinguish between a strain signal from the strain gauge representing the first deformation of the element and a strain signal from the strain gauge representing the subsequent deformation of the element; and the microprocessor being programmed to proceed with an eye examination only if a cornea contactor inserted into the holder causes the strain gauge to produce a strain signal representing the first deformation of the element.

2. The system of claim 1 wherein the cornea contactor has a location projection that detents in the holder when the cornea contactor is in the operating position.

3. The system of claim 1 wherein the element is a bendable tab and the deformation is a bending of the tab.

4. The system of claim 1 wherein the cornea contactor has a grippable tab by which the cornea contactor is inserted into the holder.

5. An eye examining instrument having a microprocessor and a cornea contactor holder combined with a molded resin cornea contactor insertable into the holder in a way that requires cornea contactor replacement before proceeding with an eye examination, the combination comprising:

the cornea contactor being molded with an element extending transversely of a direction of insertion of the cornea contactor into the holder;

the element being deformable from an initial position to a deformed position as the cornea contactor is inserted into the holder and into an operating position within the holder;

the element being configured so that a first deformation of the element requires more stress than any subsequent deformation of the element;

the holder including a strain gauge positioned to engage and deform the element as the element is inserted into the holder;

the strain gauge being arranged to produce a signal representing the strain encountered in deforming the element as the cornea contactor is inserted into the holder;

the microprocessor being programmed to recognize the strain gauge signal representing the first deformation of the element;

the microprocessor being programmed to proceed with an eye examination whenever insertion of a cornea contactor into the holder causes the strain gauge to produce the signal representing the first deformation of the element; and the microprocessor being programmed not to proceed with an eye examination whenever insertion of a cornea contactor into the holder causes the strain gauge to produce a signal distinguishably smaller than the signal representing the first deformation of the element.

6. The combination of claim 5 wherein the cornea contactor has a locator projection that seats in the holder in a detented position when the cornea contactor is in its operating position.

7. The combination of claim 5 wherein the cornea contactor has a gripping tab by which the cornea contactor is inserted into the holder.

8. The combination of claim 5 wherein the element is a hinged tab.

9. A method of ensuring that a molded resin cornea contactor is replaced in an eye examining instrument before each eye examination, the method comprising:

forming cornea contactor replacements that each have a tab that is initially deformable in response to a predetermined stress;

inserting one of the cornea contactor replacements into a cornea contactor holder of the instrument so that the deformable tab engages a strain gauge in the holder and becomes deformed by the strain gauge as the cornea contactor is moved into an operating position within the instrument;

using the strain gauge to produce a signal representing the strain encountered in initially deforming the tab as the cornea contactor is inserted into the holder;

transmitting the strain gauge signal to a microprocessor in the instrument and programming the microprocessor to recognize the strain gauge signal representing the initial deformation of the tab; and programming the microprocessor to proceed with an eye examination only upon receiving the strain gauge signal representing the initial deformation of the tab.

10. The method of claim 9 including programming the microprocessor not to proceed with an eye examination and to indicate to the instrument user upon receiving a strain gauge signal distinguishably smaller than the strain gauge signal representing initial deformation of the tab.

11. An eye examining instrument and a cornea contactor combined to ensure replacement of the cornea contactor before proceeding with examination of a pair of eyes, the combination comprising:

the cornea contactor having a deformable element configured to have a larger resistance to an initial deformation and a smaller resistance to a subsequent deformation;

the instrument having a strain gauge arranged to cause deformation of the deformable element as the cornea contactor is inserted into the instrument;

a microprocessor in the instrument receiving a deformation signal from the strain gauge and being programmed to recognize an initial deformation signal corresponding to the strain encountered during the initial deformation of the deformable element; and the microprocessor being programmed to proceed with the examination of the pair of eyes only upon receiving the initial deformation signal.

12. The combination of claim 11 wherein the deformable element is a bendable tab oriented transversely to a direction of insertion of the cornea contactor into the instrument.

13. The combination of claim 11 wherein the deformable element is configured not to break away from the cornea contactor.

14. The combination of claim 11 wherein the cornea contactor includes a location projection that snap fits into a seated position when the cornea contactor is in an operating position within the instrument.

15. A disposable molded resin cornea contactor useable in an eye examining instrument, the cornea contactor comprising:
- a bendable tab formed of the molded resin of the cornea contactor to extend from a body of the cornea contactor;
- the tab being configured to be bent from an initial position to a bent position as the cornea contactor is inserted into the instrument;
- the tab being formed to survive bending without breaking off from the cornea contactor body during insertion of the cornea contactor into the instrument and removal of the cornea contactor from the instrument for disposal; and
- the tab being formed to have a resistance to an initial bending to the bent position that is larger than any resistance of the tab to a subsequent bending to the bent position.

16. The cornea contactor of claim 15 wherein the tab is formed with a thin hinge line allowing the tab to bend.

17. The cornea contactor of claim 15 wherein the tab extends from a non-optical surface of the cornea contactor body.

18. The cornea contactor of claim 15 wherein the tab extends transversely of the direction of insertion of the cornea contactor into the instrument.

* * * * *